United States Patent [19]

Weber et al.

[11] Patent Number: 4,950,800
[45] Date of Patent: Aug. 21, 1990

[54] PROCESS FOR THE PREPARATON OF 2-METHYLBUTANAL

[75] Inventors: Jürgen Weber, Oberhausen; Peter Lappe, Dinslaken; Helmut Springer, Oberhausen, all of Fed. Rep. of Germany

[73] Assignee: Hoechst Aktiengesellschaft, Oberhausen, Fed. Rep. of Germany

[21] Appl. No.: 287,470

[22] Filed: Dec. 20, 1988

[30] Foreign Application Priority Data

Dec. 24, 1987 [DE] Fed. Rep. of Germany ....... 3744212

[51] Int. Cl.$^5$ ............... C07C 45/78; C07C 45/82
[52] U.S. Cl. .................................................. 568/492
[58] Field of Search ............................ 568/492, 449

[56] References Cited

U.S. PATENT DOCUMENTS 4,484,006 11/1984 Menapace .

FOREIGN PATENT DOCUMENTS

| 0215611 | 3/1987 | European Pat. Off. ............ 568/454 |
| 0117707 | 3/1974 | Japan .................................... 568/492 |
| 0082714 | 7/1978 | Japan .................................... 568/492 |
| 0083433 | 7/1981 | Japan .................................... 568/492 |
| 0226840 | 11/1985 | Japan .................................... 568/492 |

OTHER PUBLICATIONS

Eureopan Search Report 3 pages.
Soviet Inventions Illustrated 1983 Week 8345 (2 pages).
Soviet Inventions Illustrated 1983 Week K12 (2 pages).

Primary Examiner—Werren B. Lone
Attorney, Agent, or Firm—Jordan B. Bierman

[57] ABSTRACT

A process for the recovery of 2-methylbutanal from mixtures of isomeric aldehydes having 5 carbon atoms wherein the mixture is distilled in the presence of formaldehyde and an aldolization catalyst. The 2-methylbutanal obtained is useful as an intermediate for the preparation of various useful compounds, including the corresponding alcohol, amine, and acid.

27 Claims, No Drawings

PROCESS FOR THE PREPARATON OF 2-METHYLBUTANAL

This Application claims the priority of German Application No. P 37 44 212.0, filed Dec. 24, 1987.

The present invention is directed to a process for the separation of 2-methylbutanal from isomeric mixtures of aldehydes having 5 carbon atoms. Such mixtures frequently result from the hydroformylation of butenes and contain α unbranched aldehydes.

The desired product, is well known as an intermediate for the production of many commercially useful materials. In particular, the perfume industry oxidizes this compound to the corresponding acid which is useful in perfume manufacture.

BACKGROUND OF THE INVENTION

There are many known processes for the recovery of such aldehydes from their isomeric mixtures. For example, 2-methylbutanal can be obtained by the reaction of n-butyraldehyde with formaldehyde. The reaction is carried out in the presence of alkaline reagents, under which conditions the reactants form the 2-methylenebutanal which is partially hydrogenated to the corresponding 2-methyl compound thereafter. Although this process is capable of producing a relatively pure end product, it is extremely complicated and hence expensive to carry out. Not only is the reaction in two stages, but also the partial hydrogenation requires the use of expensive noble metal catalysts.

Another method for the production of this product is by way of hydroformylation of butene-2. Naphtha cracking produces a butene-rich fraction containing compounds having 4 carbon atoms. It is known to be a by product of the manufacture of both ethylene and gasoline, and is composed primarily of butadiene, butane, butene, and isomers thereof. In particular, n-butane, i-butane, butene-1, butene-2, and i-butene are all present to a substantial degree.

The foregoing fraction, after the butadiene and the i-butene have been largely removed, is hydroformylated to produce a mixture including aldehydes having 5 carbon atoms; e.g. n-pentanal, 2-methylbutanal, and minor amounts of 3-methylbutanal.

At present, the primary means for separating the foregoing aldehydes from one another is by fractionation. Most aldehydes exhibit great sensitivity to oxidation, condensation to form higher molecular weight products, and thermal decomposition. Therefore, it is necessary that the fractional distillation process be carried out carefully. The aldehydes must be distilled off under the mildest possible conditions and only after complete removal of the catalysts. In many cases, it is necessary (or at least desirable) to use azeotropic and/or extractive distillation to minimize or avoid the unwanted reactions which lead to decomposition and condensation.

The boiling points of the components of the fraction containing the $C_4$ compounds are extremely close together. Therefore, in order to separate them by distillation, it is necessary to have columns with extremely high separating efficiency and operate them at very high reflux ratios. These factors tend to substantially increase the cost of carrying out the separation and render such processes less economic. Moreover, there often are reductions in yield of the desired product as a result of side reactions whereby heat-sensitive, higher-boiling compounds are produced from the n-aldehydes.

In another known process, the hydroformylation of terminal olefins is carried out to produce the usual reaction mixture. The catalysts and mixture may then be separated. DE No. 24 59 152 C2 teaches that the mixture is reacted in the presence of up to a stoichiometric amount of an alkali metal hydrogen sulfite and a solvent. The sulfite precipitates the n-aldehyde as a hydrogen sulfite addition compound. This permits the precipitate to be separated, washed, and split in the usual manner.

However, because substantial manipulation of the product, as well as a considerable amount of chemicals, is required, this process is suitable primarily for the recovery of those aldehydes which are sufficiently valuable so as to justify the cost.

A thermal separation is described in DE No. 28 33 538 C2 wherein α methyl aldehydes are separated from straight-chain isomers. The aldehydes are of the formula $R-CH(CH_3)-CHO$, wherein R is a straight-chain alkyl group having 7 to 12 carbon atoms. The thermal treatment take place in the distillation column, so that both actions take place at the same time. The branched aldehydes distill over, while the straight-chain aldehydes remain with the high boiling compounds as the residue.

Another bisulfite-based process is shown in DE No. 960 187 C1. There, the isomeric aldehyde mixture is treated with an aqueous solution of a neutral sulfite and an approximately equivalent amount of a weakly acid compound. As the mixture is heated to successively higher temperatures, the aldehydes are released in the ascending order of their boiling points and can be separately withdrawn. The remaining solution, after cooling, can be reused. However, this process is useful only for the separation of the relatively-volatile lower aldehydes; the higher aldehydes tend to decompose at or about their respective boiling points, thus rendering distillation impossible or impractical.

Yet another approach is to react the mixtures with non-oxidizing strong mineral acids. Under such circumstances, the process (as shown in DE No. 22 18 305) converts the straight-chain aldehydes into 1,3,5-trioxanes. These can then be separated by fractional crystallization. Thereafter, the trioxanes are placed in a distillation apparatus in the presence of small amounts of phosphoric oxide, thereby depolymerizing them.

As can readily be appreciated, this method requires different crystallizabilities and solubilities of the trimers of the n-alkanals and i-alkanals. When both are crystalline, the process is inoperable; as a result, the usefulness of this process is severely limited.

BRIEF DESCRIPTION OF THE PRESENT INVENTION

It is, therefore, among the objects of the present invention to provide a method for recovering 2-methylbutanal from a mixture of its isomeric aldehydes. Such mixtures are principally those which result from the hydroformylation of butenes.

In essence, the present process comprises the distillation of a mixture of isomeric aldehydes in the presence of both formaldehyde and an aldolization catalyst. The mixture usually includes α-unbranched aldehydes, such aldehydes being those wherein the carbon atom adjacent the aldehyde group carries only hydrogen. In particular, n-pentanal and 3-methylbutanal are present.

Those aldehydes having, for example, a methylene group α to the aldehyde group react catalytically with formaldehyde to form the corresponding 2-methylene aldehydes. Such reactions are usually carried out at elevated pressures and exhibit wide variations in residence periods; e.g. from a few seconds to several hours. Aldehydes having a single hydrogen atom on the α-carbon undergo a similar reaction with formaldehyde to produce the corresponding α-methylol compound.

Thus, it is recognized that the α-unbranched aldehydes and the α-mono-branched aldehydes are highly reactive. Therefore, it was not to be expected that such aldehydes could be selectively reacted in order to separate them from their mixtures.

In addition, it is recognized that mixtures having a high percentage of $C_4$ hydrocarbons, particularly those including butenes, are readily susceptible of hydroformylation. Such mixtures result, for example, from naphtha cracking. In this situation, the olefins are further concentrated as, by removal of the butadiene or by conversion of the isobutene to methyl t-butyl ether. A specific example of such butane-rich mixtures is raffinate II. This normally has approximately the following composition.

| Constituents | Raff. II vol. % |
|---|---|
| Isobutane | 3–8 |
| Isobutene | 0.5–1.5 |
| 1-butene | 10–15 |
| n-butane | 19–26 |
| 2-butene(cis/trans) | 52–65 |

As will readily be appreciated, the new process is not limited to the foregoing starting materials. Any butene-containing mixture is satisfactory for hydroformylation followed by the reaction-distillation method of the present invention. Hydroformylation itself is well known in the art as set forth in Chemiker Z. 96 (1972), page 383 et seq. and in DE No. PS 26 27 354. See also Ullmann's Encyclopedia of Industrial Chemistry, 5th Edition (1985), Vol. A 4, page 488.

Specifically, the hydroformylation of raffinate II is carried out with cobalt as the catalyst at 110° to 180° C. under 20 to 30 MPa. The catalyst is separated by treating the product with water, oxidizers, acidic agents, and/or other usual additives. This results in a mixture of the composition

| $C_4$ hydrocarbons | 10–15% by weight |
|---|---|
| 2-methylbutanal | 18–25% by weight |
| n-pentanal | 40–50% by weight |
| 3-methylbutanal | 0.5–1.5% by weight |
| others | 15–21% by weight |

After distilling off the hydrocarbons and the fraction containing the aldehydes having 5 carbon atoms, the composition is

| 2-methylbutanal | 80–95% by weight |
|---|---|
| 3-methylbutanal | 2–5% by weight |
| n-pentanal | 5–15% by weight |

The residue of the distillation step is principally n-pentanal.

The foregoing fraction is then reacted with one to two mols of formaldehyde per mol of α-unbranched aldehydes (n-pentanal and 3-methylbutanal). Preferably, 1.1 to 1.4 mols of formaldehyde are used per mol of α-unbranched aldehydes. The formaldehyde is advantageously used in water solution, but solutions in other solvents such as also alcohol are also satisfactory. Paraformaldehyde is also suitable. While it has been found desirable to add the entire amount of formaldehyde to the reaction mixture at the beginning, it may also be added portionwise over the course of the reaction.

The desired reaction is catalyzed by the presence of amines. In particular, secondary amines of the formula $$R^1-NH-R^2$$

In the foregoing formula, $R^1$ and $R^2$ are individually alkyl groups having 1 to 12 carbon atoms. Preferably, the alkyl groups have 3 to 5 carbon atoms, and d-n-butylamine has been found most suitable.

A further preferred form of the invention carries out the foregoing reaction in the presence of monocarboxylic acids having 1 to 10 carbon atoms or polycarboxylic acids having 2 to 10 carbon atoms. The mono and polycarboxylic acids can be aromatic, araliphatic, and aliphatic. Both monocarboxylic acids having 3 to 5 carbon atoms and aliphatic carboxylic acids in general are preferred. Worthy of particular note are acetic acid, propionic acid, n-butyric acid, i-butyric acid. Most preferable is n-butyric acid.

As to the amine catalyst, 0.025 to 0.3 mols per mol of α-unbranched aldehydes is used. The preferred range is 0.1 to 0.2. Insofar as the carboxylic acids are concerned, 0.05 to 0.5 equivalents per mol of α-unbranched aldehydes has been found staisfactory. However, it is preferable to maintain the acid concentration between 0.15 and 0.3 equivalents per mol of α-unbranched aldehydes.

It is believed that the mechanism of the reaction is such that the α-unbranched aldehydes are converted by the formaldehyde to α-methylol aldehydes. These compounds are generally unstable and autoconvert to the corresponding α-methylene aldehydes (acroleins) with the formation of water. Since the boiling points of these methylene aldehydes are quite different from that of the methyl aldehyde, it is easy to separate them by distillation.

It is a feature of the present invention that the reaction of the aldehyde mixture with formaldehyde is carried out during distillation. The equipment required is not critical and the existing types are quite satisfactory for carrying out the present process. Such distillation columns having glass rings or metal coils as packing material have been found suitable. Generally, the columns have 9 to 72 theoretical plates, while the preferred range is 24 to 36. The reflux ratio will depend upon the type of column used, but is well within the ability of the person of ordinary skill to determine. It has been found that a packed column having 24 theoretical plates operates well with five parts reflux to one part product. Similarly, the temperatures are readily determined by the person of ordinary skill. With respect to the column previously described, the temperature of the bottom product will be up to about 120° C. at atmospheric pressure.

It has been found that, in accordance with the present process, the 2-methylbutanal can be obtained in purities of 97% to 99%. The only contaminants are small amounts of 3-methylbutanal, traces of n-pentanal, and some inert components. However, the latter in no way impair further processing of the 2-methylbutanal to form other products; e.g. acids, amines, alcohols, etc. Moreover, these inert substances are easily separated from the foregoing classes of derivatives.

The following Example is intended to illustrate the invention, without being limitative.

EXAMPLE

Raffinate II containing about 7% by volume of i-butane, 25% by volume of n-butane, 15% by volume of 1-butene, 52% by volume of 2-butene and 1% by volume of i-butene is hydroformylated at about 150° C. and at a synthesis gas pressure (CO: $H_2 = 1:1$) of about 22 MPa in the presence of a cobalt catalyst. The pressure is released and the product is freed from the catalyst. This mixture is distilled to obtain a fraction boiling at between about 86° and about 93° C. and with the following composition (% by weight):

| First runnings: | 1.2% |
|---|---|
| 3-methylbutanal: | 3.2% |
| 2-methylbutanal: | 83.4% |
| n-pentanal: | 11.2% |
| Final runnings: | 1.0% |

2000 g of this aldehyde mixture (3.33 moles of α-unbranched aldehydes) are mixed with 399.4 g of an aqueous formaldehyde solution containing 35% by weight of formaldehyde (4.66 moles), 64.5 g of di-n-butylamine (0.5 moles), and 59.0 go of n-butyric acid (0.67 moles) and subjected to discontinuous fractional distillation. The packing column used has 24 theoretical plates, the reflux ratio is 5 parts reflux to one part overhead product removed.

At a head temperature of 79° C. maximum and a bottom temperature of 102° C. maximum the main fraction consists of 1582.3 g of organic product and 258.6 g of water phase.

According to gas chromatography analysis the organic product has the following composition (% by weight):

| First runnings: | 1.36% |
|---|---|
| 3-methylbutanal: | 0.03% |
| 2-methylbutanal: | 97.14% |
| n-pentanal: | — |
| i-propylacrolein: | 0.05% |
| Final runnings: | 1.42% |

92.1% by weight of the 2-methylbutanal used is thus recovered from the main fraction in virtually isomer-free form. Further amounts of 2-methylbutanal can be obtained from the higher-boiling fractions.

The product is suitable for the direct preparation of secondary compounds such as 2-methylbutylamine, 2-methylbutanol and 2-methylbutyric acid. It is recovered in a purity of 99% by simple redistillation.

While only a limited number of specific embodiments of the present invention have been expressly described, it is, nonetheless, to be broadly construced and not to be limited except by the character of the claims appended hereto.

What we claim is:

1. A process for recovering 2-methylbutanal from a mixture of $C_5$ aldehydes comprising; adding formaldehyde to said mixture and distilling in the presence of an aldolization catalyst of the formula $$R^1-NH-R^2$$

wherein $R^1$ and $R^2$ are individually alkyl having 1 to 12 carbon atoms.

2. The process of claim 1 wherein said mixture results from hydroformylation of at least one butene.

3. The process of claim 1 wherein said mixture includes α-unbranched aldehydes, there being from 1 to 2 mols of said formaldehyde per mol of said unbranched aldehydes.

4. The process of claim 3 wherein there is from 1.1 to 1.4 mols of said formaldehyde per mol of said unbranched aldehydes.

5. The process of claim 3 wherein said unbranched aldehydes comprise n-pentanal and 3-methylbutanal.

6. The process of claim 1 wherein said formaldehyde is in water solution.

7. The process of claim 1 wherein said formaldehyde is polymerized.

8. The process of claim 7 wherein said formaldehyde is paraformaldehyde.

9. The process of claim 1 wherein said catalyst is an amine.

10. The process of claim 9 wherein said amine is secondary.

11. The process of claim 1 wherein said alkyl has 3 to 5 carbon atoms.

12. The process of claim 11 wherein $R^1$ and $R^2$ are n-butyl.

13. The process of claim 1 wherein said formaldehyde is added stepwise.

14. The process of claim 13 wherein at least one carboxylic acid is added to said mixture.

15. The process of claim 14 wherein said acid is monocarboxylic.

16. The process of claim 15 wherein said acid has 1 to 10 carbon atoms.

17. The process of claim 14 wherein said acid is polycarboxylic.

18. The process of claim 17 wherein said acid has 2 to 10 carbon atoms.

19. The process of claim 16 wherein said acid has 3 to 5 carbon atoms.

20. The process of claim 14 wherein said acid is aromatic, araliphatic, or aliphatic.

21. The process of claim 20 wherein said acid is aliphatic.

22. The process of claim 21 wherein said acid is taken from the class consisting of acetic acid, propionic acid, n-butyric acid, i-butyric acid, oxalic acid, succinic acid, and tartaric acid.

23. The process of claim 22 wherein said acid is n-butyric acid.

24. The process of claim 9 wherein said mixture includes α-unbranched aldehydes, there being from 0.025 to 0.3 mols of said amine per mol of said unbranched aldehyde.

25. The process of claim 24 wherein there is from 0.1 to 0.2 mols of said amine per mol of said unbranched aldehydes.

26. The process of claim 14 wherein said mixture includes α-unbranched aldehydes, there being from 0.05 to 0.5 equivalents of said acid per mol of said unbranched aldehydes.

27. The process of claim 26 wherein there is from 0.15 to 0.03 equivalents of said acid per mol of said unbranched aldehydes.

* * * * *